United States Patent [19]

Woodward

[11] Patent Number: 5,088,924
[45] Date of Patent: Feb. 18, 1992

[54] DENTAL FIBEROPTIC HANDPIECE HOSE ASSEMBLY AND METHOD

[76] Inventor: Gary Woodward, 9301 S.W. Sagert, Apt. 29, Tualatin, Oreg. 97062

[21] Appl. No.: 576,272

[22] Filed: Aug. 31, 1990

Related U.S. Application Data

[63] Continuation of Ser. No. 317,833, Mar. 1, 1989, Pat. No. 4,975,058.

[51] Int. Cl.$^5$ .............................................. A61C 1/08
[52] U.S. Cl. ...................................... 433/126; 433/29
[58] Field of Search ....................... 433/29, 229, 126; 606/15, 16; 350/96.24

[56] References Cited

U.S. PATENT DOCUMENTS

| | | | |
|---|---|---|---|
| 3,614,414 | 10/1971 | Gores | 433/29 X |
| 3,758,951 | 9/1973 | Scrivo et al. | 433/29 |
| 3,858,577 | 1/1975 | Bass et al. | 606/15 X |
| 4,080,737 | 3/1978 | Fleer | 32/22 |
| 4,182,038 | 1/1980 | Fleer | 433/85 |
| 4,260,382 | 4/1981 | Thomson | 433/126 |
| 4,303,392 | 12/1981 | Rollofson | 433/126 |
| 4,334,863 | 6/1982 | Magid et al. | 433/29 |
| 4,521,189 | 1/1985 | Lares et al. | 433/84 |
| 4,530,568 | 7/1985 | Haduch et al. | 128/397 X |
| 4,541,802 | 9/1985 | Olsen | 433/126 |
| 4,553,938 | 11/1985 | Olsen | 433/126 |
| 4,578,033 | 3/1986 | Mossle et al. | 433/126 X |
| 4,844,062 | 7/1989 | Wells | 606/16 |
| 4,890,898 | 1/1990 | Bentley et al. | 606/16 |

FOREIGN PATENT DOCUMENTS

| | | | |
|---|---|---|---|
| 0017318 | 10/1980 | European Pat. Off. | 17/96 |
| 1349227 | 4/1974 | United Kingdom | 128/ |

*Primary Examiner*—Robert P. Swiatek
*Assistant Examiner*—Nicholas B. Lucchesi
*Attorney, Agent, or Firm*—Quirk, Tratos & Roethel

[57] ABSTRACT

A fiberoptic dental headpiece hose assembly has a smooth-walled, aseptic outer tubing that contains a plurality of internal components to provide drive air, an exhaust line, chip air and coolant water to the dental handpiece. The fiberoptic handpiece hose assembly is field-serviceable due to the rearend release connection of the outer tubing to the swivel assembly. This permits access to the internal components to allow repairs to be made in the dentist's office. The fiber-optic bundle is made from an acrylic material and the adapter is made generally from plastic to reduce the overall weight of the assembly and to improve the reliability and service life of the assembly.

17 Claims, 3 Drawing Sheets

DENTAL FIBEROPTIC HANDPIECE HOSE ASSEMBLY AND METHOD

CROSS-REFERENCE TO RELATED APPLICATION

This application is a Continuation of application Ser. No. 07/317,833, filed Mar. 1, 1989, now U.S. Pat. No. 4,975,058.

BACKGROUND OF THE INVENTION

This application relates to dental fiberoptic handpiece hose assemblies, and more particularly to dental fiberoptic handpiece hose assemblies that are field-serviceable.

In the modern dental office, one of the main pieces of equipment used by the dentist is the handpiece. The handpiece is connected to its power supply by a long, flexible hose. The hose contains parallel passageways for transmitting drive air, exhaust air, chip air, water and light to the handpiece.

A typical commercially available hose has four passageways for the air and liquid transmissions and a fifth central passageway containing a fiberoptic bundle for transmitting light to an illuminator located in the handpiece to provide extra light to assist the dentist during the cutting, polishing or other activities in the patient's oral cavity. Another conventional hose comprises a flexible outer tube, often cloth-covered, that contains a plurality of separate conduits or tubings for transmitting the air, water and light to the handpiece.

Representative of these conventional assemblies is that shown in U.S. Pat. No. 4,553,938 (Olsen).

There is a need in the dentist office for a handpiece hose assembly that is aseptic. Because of the concern regarding the transmission of communicable diseases, especially the Acquired Immune Deficiency Syndrome, extra precautions are being taken to ensure that all dental treatments are as sanitary as possible. There is a renewed emphasis on providing equipment that is aseptic—that is, the equipment needs to be as bacteria free as possible. The hose needs to be cleaned on a regular basis and should be of a construction that does not contain crevices or areas in which bacteria can collect.

During dental operations the handpiece is often twisted, rotated or reoriented to allow the dentist to work at all angles in the patient's oral cavity. In order to permit this twisting, rotating and reorientation, the hose needs to be attached to the handpiece by a swivel arrangement. Various assemblies have been proposed to allow for a maximum amount of swiveling, such as the assembly shown in the above-referenced Olsen patent.

Also during use of the dental handpiece, it is a common occurrence that leaks or blockages will occur in the fluid lines that transmit the air and water to the handpiece. It would be preferable if the fiberoptic handpiece and hose could be serviced in the field—that is, in the dentist's office—without the necessity of simply replacing the entire assembly or returning the assembly to the repair shop, neither of which is cost effective. Because returning the parts to the repair shop is not cost effective, the current practice is to simply replace the entire hose assembly rather than repairing it at all.

The conventional fiberoptic bundle is made of glass fibers and is also a problem area in that it is relatively quite heavy and non-flexible. The weight of the fiberoptic bundle increases the fatigue encountered by the dentist during his workday. The non-flexibility of the fiberoptic bundle increases the likelihood of breaks occurring in the fiberoptic line during the twisting, rotating and reorientation of the hose that occurs during the use of the handpiece.

Many conventional fiberoptic handpieces are also touch-activated—that is, the fiberoptic bundle is activated by the touch of the operator to transmit light to the handpiece. This is accomplished by the use of a metal adapter mounted in the connection between the hose and the handpiece. The fiberoptic bundle is attached to the metal adapter and the adapter detects the touch of the operator to activate the fiberoptic bundle which causes light to be transmitted to the handpiece. The use of metal, however, in the adapter adds to the overall weight of the assembly.

It is an object of the present invention to provide for an aseptic hose that can be used in a dental fiberoptic handpiece assembly.

It is a feature of the present invention that the hose used in a dental fiberoptic handpiece assembly has no external ridges or crevices that may trap bacteria and the assembly may be easily cleaned by simply wiping with cleaning fluid.

It is an advantage of the present invention that the aseptic hose will drastically eliminate the potential for bacteria to be present on the hose thereby decreasing the likelihood that communicable diseases might be encountered in the dentist's office.

It is a further object of the present invention that the dental handpiece can be connected to the hose by an assembly that is field-serviceable.

It is a further feature of the present invention that the connection between the hose and the dental handpiece is releasable to allow access to the internal components to permit servicing in the field. The hose is attached to the rear end of the swivel assembly to allow easy access to the internal components of the assembly.

It is an further advantage of the present invention that leaks or blockages in the air or liquid transmitting components or breakages in the fiberoptic bundle can be repaired in the field without the necessity of replacing the entire assembly or returning the entire assembly to the repair shop.

It is a further object of the present invention to provide an improved fiberoptic bundle that is more flexible and lightweight than the presently used fiberoptic bundles.

It is a further feature of the present invention to utilize a fiberoptic bundle made from an acrylic material.

It is a further advantage of the present invention that the acrylic fiberoptic bundle will provide an assembly that is lighter in weight and more flexible than the fiberoptic bundles presently used thereby increasing the ease of use of the handpiece and also reducing the potential for breakdown of the fiberoptic hose assembly.

It is a further object of the present invention to provide an improved touch-activated adapter that activates the fiberoptic bundle to provide light to the dentist's working area.

It is a further feature of the present invention to utilize a generally plastic touch-activated adapter to activate the fiberoptic bundle.

It is a further advantage of the present invention that the generally plastic touch-activated adapter for the fiberoptic bundle will decrease the weight of the overall assembly.

It is a further object of the present invention to provide a fiberoptic hose assembly that is oil resistant.

It is a further feature of the present invention to utilize an outer tubing material that is resistant to the lubricant oil that is present in the turbine-powered handpiece.

It is a further advantage of the present invention that the oil resistant outer tubing will resist hardening and cracking and provide for an improved life of the fiberoptic handpiece hose assembly.

SUMMARY OF THE INVENTION

A dental fiberoptic handpiece hose assembly comprises a flexible, aseptic outer tubing that contains internally a plurality of conduits and wires for the drive air, exhaust air, coolant water and "chip" air, as well as a fiberoptic bundle and a sensing cable. An alternative embodiment utilizes an extruded tubing that has internal, integral passageways for the drive air, exhaust air, chip air and coolant water, as well as cavities through which the fiberoptic bundle and the sensing cable can be run. The outer surface of either tubing is quite regular without any crevices that would trap bacteria. The fiberoptic bundle comprises an acrylic material that is lightweight and flexible. A generally plastic adapter is utilized to activate the fiberoptic bundle by the touch of the operator. The connection between the handpiece and the hose can be swivelable or non-swivelable.

DETAILED DESCRIPTION OF THE PREFERRED EMBODIMENTS

The present invention relates to a fiberoptic hose assembly that is utilized in conjunction with a conventional dental handpiece that utilizes fiberoptics. The handpiece is the device that is held in the hand of a dentist when he is performing certain dental operations in the oral cavity of a patient. These operations typically include drilling and filling cavities as well as cleaning teeth. The handpiece is an air-driven, turbine-powered device to which is attached the appropriate tool to allow the dentist to perform his operations. The hose assembly connects the handpiece to the power supply which is located in a remote area of the dentist's office. Because the dentist works at a variety of angles to the oral cavity of the patient, it is preferable that the connection between the handpiece and the hose assembly be swivelable, although it is quite common that the hose assembly is connected to the handpiece in a non-swivelable manner.

The general working environment of the present invention is shown in U.S. Pat. No. 4,553,938 (Olsen), the disclosure of which is hereby incorporated by reference herein.

Figure 1:
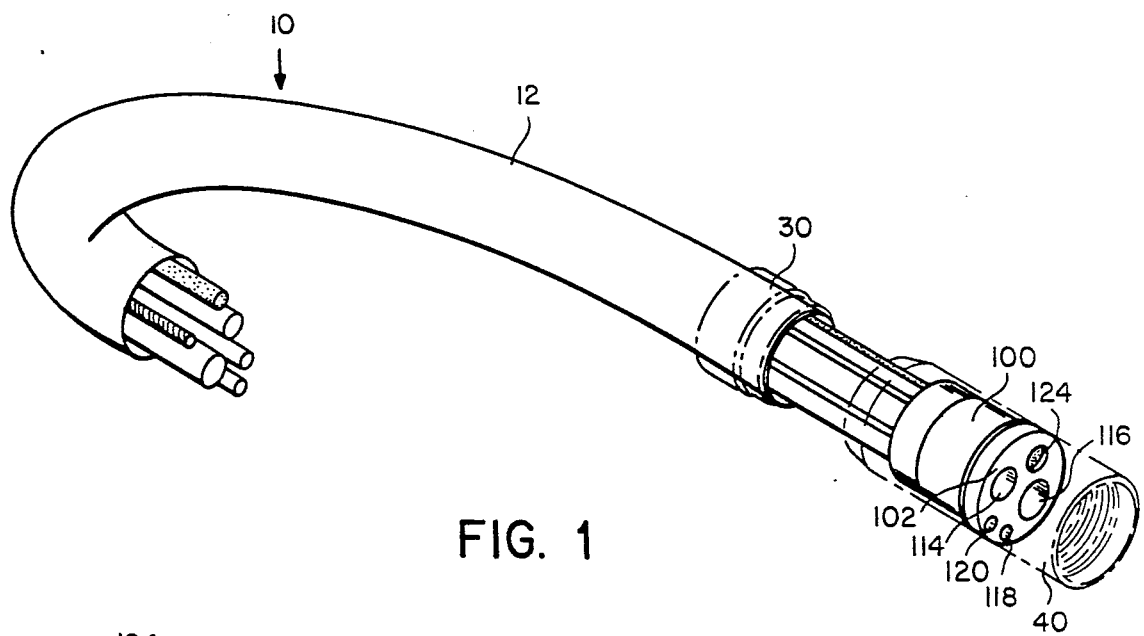
FIG. 1 is a perspective view of the apparatus of the present invention.
Figure 2:
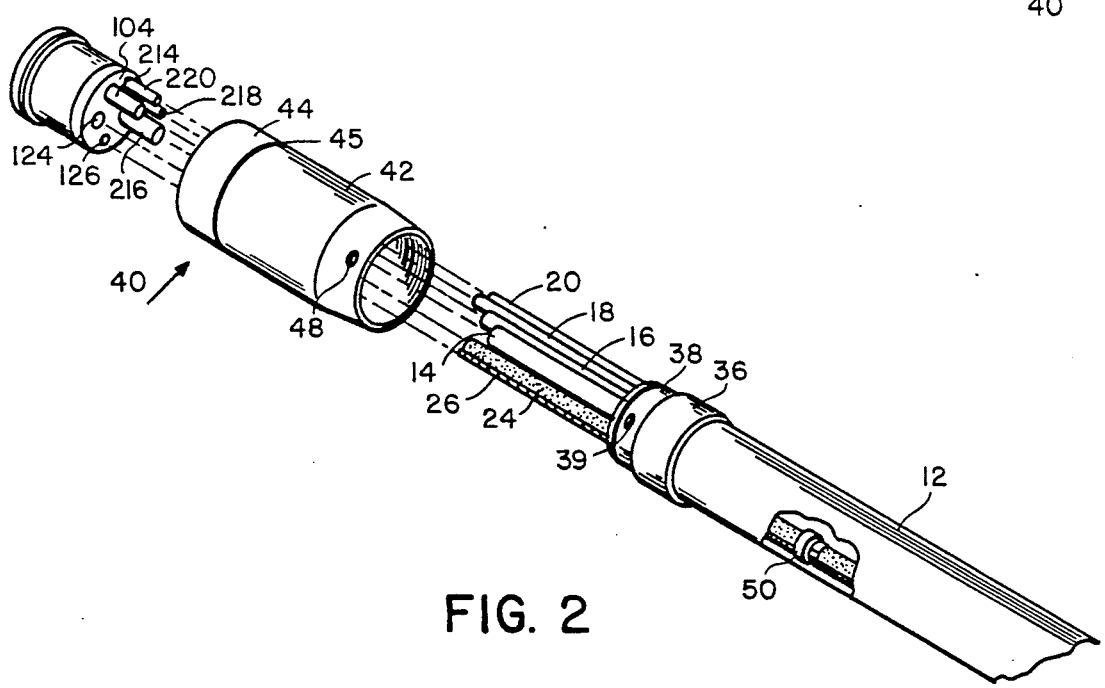
FIG. 2 is an exploded view of the apparatus of the present invention.

As shown in FIGS. 1 and 2 of the drawings, the fiberoptic hose assembly 10 of the present invention comprises a smooth-walled rubber or plastic outer tubing 12. The outer tubing 12 is quite flexible and smooth on both its inner and outer surfaces. Inside the outer tubing 12 are contained a plurality of components that are used to feed air, water and light to the handpiece.

A first inner tubing 14 carries the drive air which operates the turbine in the handpiece to cause the tool connected to the handpiece to rotate at the high speeds required by modern dentistry. A second inner tubing 16 is the exhaust line for withdrawing the drive air from the handpiece. A third inner tubing 18 delivers "chip air" to the patient's oral cavity which is used to loosen debris that occurs during the drilling process. A fourth inner tubing 20 delivers coolant water to the patient's oral cavity. A fiberoptic bundle 24 is also contained in the tubing along with a sensing cable 26. Each of these six components are easily provided inside the outer tubing 12. The outer tubing 12 being thin-walled and flexible makes it very easy to feed each of these components down the length of the outer tubing 12.

Figure 5:
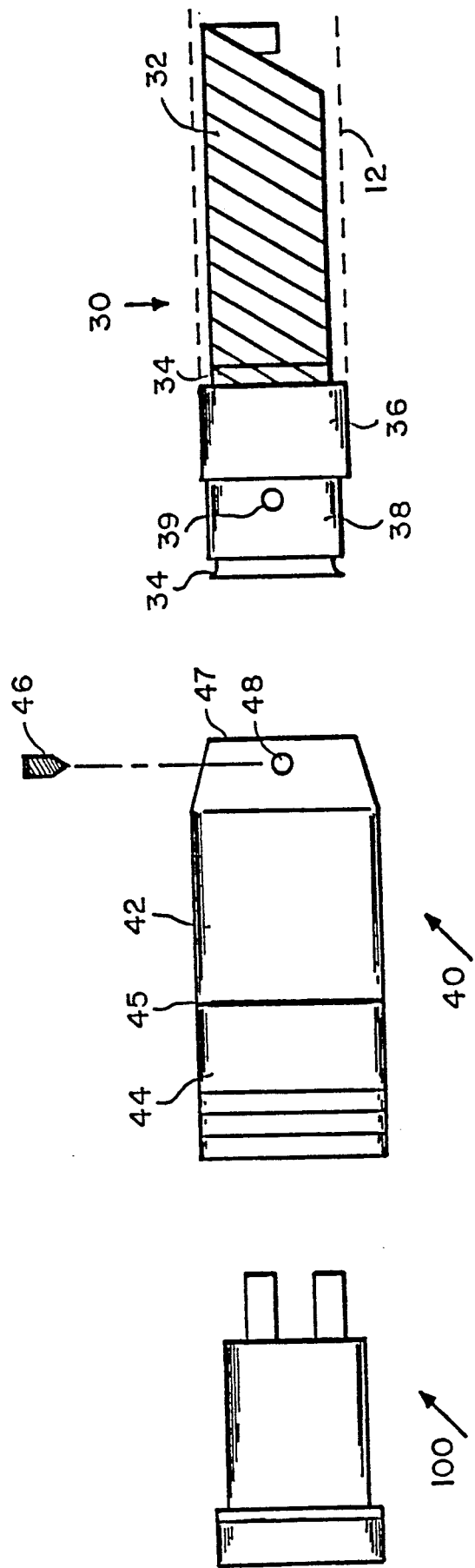
FIG. 5 shows an exploded view of the outer tubing retainer, the swivel member and the adapter of the present invention.

As shown in phantom in FIG. 1 and in more detail in FIG. 5, the outer tubing 12 is provided at its end adjoining the handpiece with an outer tubing retainer 30. The outer tubing retainer 30 is comprised of an inner plastic hollow spring 32 that functions to support the circular cross-section of the outer tubing 12. The spring 32 is press fit over the end of a hollow metal inner retainer 34. A retainer endpiece 36 is likewise press fit over the spring 32 so that the spring is firmly held in place between the inner retainer 34 and the retainer endpiece 36. The outermost portion of the retainer endpiece 36 is a stepped flange 38 that functions as a locking surface for the swivel member 40 as will be more fully explained herein.

The swivel member 40 is a hollow metal component comprised of a rear swivel piece 42 and a front swivel piece 44 joined together at a swivel connection 45 in a conventional manner. The open end 47 of the rear swivel piece 42 is press fit onto the stepped flange 38 of the retainer endpiece 36. This press fit connection is more securely held in place by the provision of a set screw 46 that threads through an aperture 48 in the rear swivel piece 42 and abuts into an indent 39 in the retainer endpiece 36. This arrangement locks the swivel member 40 to the retainer 30.

Mounted inside the front swivel piece 44 is the adapter 100. The interior components of the outer tubing 12 are each individually connected to the adapter 100. The adapter 100 is a generally plastic piece that has a plurality of passageways therethrough. The passageways correspond to the air, water and light components contained within the outer tubing 12. As shown in FIG. 1, the exit end 102 of the adapter 100 acts as a "socket" into which is "plugged" the handpiece. The drive air passageway 114, the exhaust air passageway 116, the "chip" air passageway 118, the coolant water passageway 120 and the fiberoptic bundle passageway 124 all correspond and line up with the respective openings for the same items in the handpiece. The sensing cable 26 terminates in the adapter 100 which will be more fully explained in connection with FIG. 3.

The entrance end 104 of the adapter 100, as shown in FIG. 2, is provided with a plurality of stems that act as the joining means for the air, water and light components contained in the outer tubing 12. In use, stem 214 is the connection for the drive air tubing 14; stem 216 is the connection for the exhaust air tubing 16; stem 218 is the connection for the "chip" air tubing 18 and stem 220 is the connection for the coolant water tubing 20. Each stem is formed in the shape of a barb as disclosed and shown in the Olsen patent, above.

The fiberoptic hose assembly shown in FIGS. 1 and 2 is "field-serviceable." This means that repairs to the fiberoptic hose assembly can be made in the dentist's office without the necessity of returning the entire assembly to the repair shop. In use, leaks or blockages will typically occur at or close to the location where the tubings connect to the adapter 100. In order to repair these leaks or blockages, the repair person must have access to the adapter 100 and to the tubings connected to the adapter 100. Access is achieved by loosening the set screw 46 which allows the rear swivel piece 42 of the swivel member 40 to be slid off the stepped flange 38 of the retainer endpiece 36. Because there is slack in the tubings contained within the outer tubing 12, both the adapter 100 and the tubings connected thereto can be moved slightly apart from the swivel member 40 to allow the repair person to inspect the junctions of each tubing with its associated stem to determine if a leak or blockage is present. For example, if a leak or blockage is present in the coolant water tubing 20, it is simple matter for the repairman to clean out the blockage or repair the leak and then reconnect the coolant water tubing 20 to the stem 220. There is enough slack in the length of the water tubing 20 contained in the outer tubing 12 to permit a portion of the water tubing 20 to be removed and the remainder of the water tubing to be reconnected to the stem 220. Repairs to each of the other components can be effected in a similar manner.

One particular advantage of this assembly arrangement is that the fiberoptic bundle 24 is also accessible to the repair person when the swivel member 40 is slid off the stepped flange 38 of the retainer endpiece 36. The fiberoptic bundle 24 can also be separated from the fiberoptic bundle passageway 120 in the adapter 100. After removal, the fiberoptic bundle 24 can be utilized as a light source by the repair person to help look at and inspect the other tubings to determine the source of the leak or blockage. Another advantage of this construction is that the fiberoptic bundle 24 can be released from the adapter 100 and moved slightly out of the way while the repairs are made. This minimizes the possibility of causing damage to the fiberoptic bundle 24 during repairs. This is particularly important since the fiberoptic bundle 24 is usually quite fragile.

In the preferred embodiment, a plastic connecting clip 50 holds the fiberoptic bundle 24 to the sensing cable 26 inside the outer tubing 12. The clip 50 is located, preferably, approximately one foot from the handpiece end of the outer tubing 12. The purpose of the clip 50 is to prevent the fiberoptic bundle 24 from sliding down the inside of the outer tubing 12 when the fiberoptic bundle 24 is removed from the adapter 100 during repair work.

Once the necessary repairs have been completed, it is a simple matter for the repair person to reconnect all of the tubings to their respective stems in the adapter 100. The fiberoptic bundle 24 is then reinserted into the fiberoptic bundle passageway 124 in the adapter 100 and the adapter is slid back into the swivel member 40 and locked in place to the stepped flange 38 of the retainer endpiece 36 by means of the set screw 46.

The fiberoptic hose assembly of the present invention as shown in FIGS. 1 and 2 is also an aseptic design—that is, the design of the fiberoptic hose assembly is intended to inhibit and minimize the possibility of bacteria collecting on the surfaces of the fiberoptic hose assembly. The outer tubing 12 is completely smooth-walled and does not have any creases, bends or surface irregularities that would provide locations at which bacteria could collect. The smooth-walled configuration of the outer tubing 12 makes cleaning quite easy.

An alternative embodiment of the invention shown in FIGS. 1 and 2 involves the same field-serviceable, aseptic design without a swivel member 40. Instead the swivel member 40 is replaced with a one-piece member that is connected to the outer tubing 12 by means of the same retainer endpiece 36 and then also has an adapter 100 mounted therein.

Figure 3:
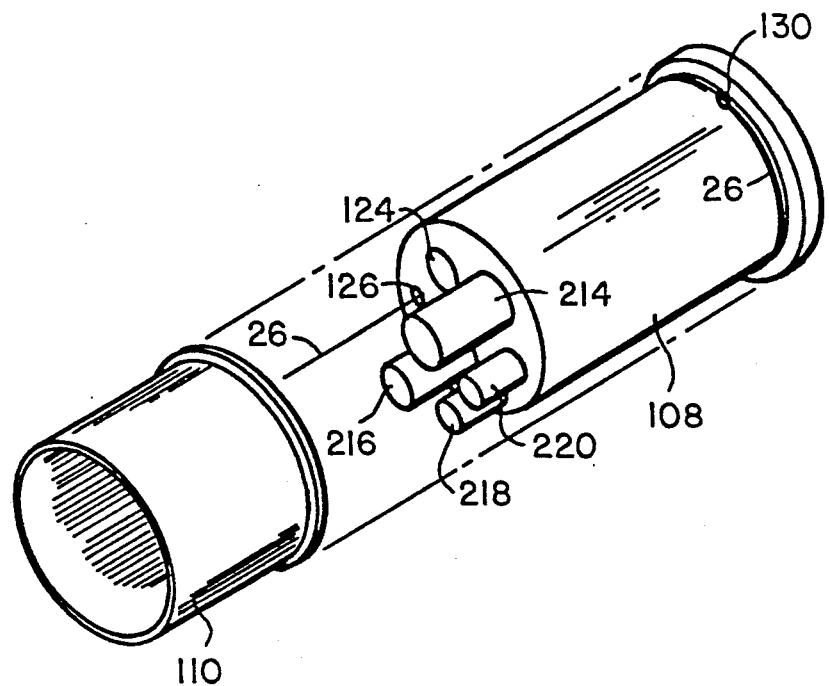
FIG. 3 shows the adapter of the present invention in an exploded view.

FIG. 3 shows another feature of the present invention. In conventional hose assemblies, the adapter is made entirely of metal. In the present invention, the adapter 100 has a metal sleeve 110 that slides over the generally plastic body portion 108. This metal sleeve 110 functions as the contact point for the touch-activation system that turns on and off the fiberoptic bundle 24. The use of a plastic adapter reduces the overall weight of the handpiece tubing assembly which mitigates the fatigue realized by the dentist during a long session of working on a patient. The plastic body portion 108 of the adapter 100 is provided with an internal passageway 126. This internal passageway 126 terminates in the surface of the plastic body portion 108 at an aperture 130. In the preferred embodiment, the aperture 130 is located near the end of the plastic body portion 108 as shown in FIG. 3, although the location of this aperture 130 can be at any point along the surface of the plastic body portion 108. The end of the sensing cable 26 is fed through the passageway 126 of the plastic body portion 108 until the sensing cable comes out the aperture 130. The end of the sensing cable 26 is then wrapped around the plastic body portion 108 to secure the sensing cable to the plastic body portion 108. The metal sleeve 110 is then slid over the plastic body portion 108 to secure the sensing cable 26 in place. The metal sleeve 110 also forms an electrical connection with the sensing cable 26 to provide for the touch-activation of the fiberoptic bundle 24 in a manner known in the art. The use of plastic for the body portion 108 of the adapter 100 reduces the overall weight of the fiberoptic handpiece assembly 10.

Figure 4:
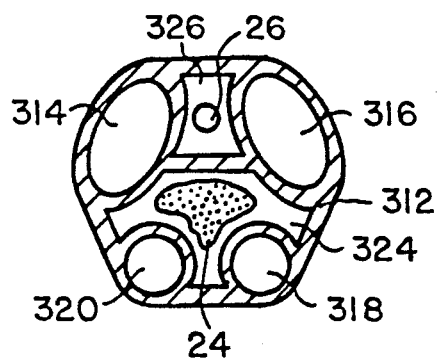
FIG. 4 shows in cross-section an alternate embodiment of the present invention.

Another embodiment of the invention is shown in FIG. 4. Instead of using an outer tubing which contains a plurality of inner tubings and wires, the outer tubing itself comprises an extruded member that has a plurality of integral passageways formed therein. As depicted in FIG. 4, the outer tubing 312 is manufactured by extrusion with a series of internal dividers that form a plurality of passageways. Passageway 314 conducts the drive air, passageway 316 handles the exhaust air, passageway 318 conducts the "chip" air, passageway 320 conducts the coolant water, passageway 324 provides a cavity through which is run the fiberoptic bundle 24 and passageway 326 provides a separate cavity through which is run the sensor cable 26. The outer surface of the tubing 312 is smooth-walled and aseptic. This tubing configuration was designed and is sold by Coaxco, Inc., P.O. Box 489, Tualatin, Oreg. 97062. This embodiment contemplates using the tubing 312 in place of the outside tubing 12 and inner tubings and wires 14 16, 18, 20, 24 and 26 shown in FIGS. 1 and 2. The end of tubing 312 will connect with the adapter 100 through the use of the swivel assembly 40.

Another advantage that is derived from using the tubing 312 made by Coaxco, Inc. is that this tubing 312 is oil resistant. During use of a turbine-powered handpiece, the lubricant oil used in the handpiece has a tendency to mix with the exhaust air carried in the passageway 316. Tubing that is made from oil resistant material will resist hardening and cracking caused by the reaction of the lubricant oil with the tubing material. Oil resistant tubing provides for an improved life of the fiberoptic handpiece assembly.

In order to run the fiberoptic bundle 24 through the passageway 324, it is necessary to expand the diameter of the passageway 324. Air is applied to the passageway 324 which expands the diameter of the passageway 324 to a larger size. While the passageway 324 is expanded, it is a simple matter to feed the fiberoptic bundle 24 down the passageway 324. When this feeding is completed, the expansion air is removed which permits the passageway 324 to return to its normal diameter. The fiberoptic bundle 24 is then compressed by the walls of passageway 324 and the fiberoptic bundle is actually deformed into the cross-sectional shape shown in FIG. 4. This deformation of the fiberoptic bundle 24 inhibits the fiberoptic bundle from twisting within the outer tubing 312 when the fiberoptic handpiece assembly is used by the dentist. In a conventional assembly, the fiberoptic bundle is subjected to twisting stress and strain during use which leads to cracking and breaking of the fiberoptic bundle. Any cracking or breaking of the fiberoptic bundle limits the ability of the fiberoptic bundle to transmit light. Thus the design of the present invention improves the longevity and usefulness of the fiberoptic bundle 24 which improves the utility of the entire fiberoptic handpiece hose assembly.

The fiberoptic bundle 24 can be made from the conventional glass fiberoptic material that is currently in use. The fiberoptic bundle 24 is made up of a plurality of glass fibers having the property of transmitting light. Each glass fiber has a typical cross-section of approximately 0.001 inches. The resulting fiberoptic bundle has an overall diameter of generally between 0.073 and 0.093 inches.

As an alternative to the glass fiberoptic bundles currently in use, the fiberoptic bundle 24 is preferably made of an acrylic material that will transmit light. Suitable acrylics that can be used as the fiberoptic bundle are manufactured under the tradename LUMILEEN by Poly-optical Products, Inc, 1815 Carnegie Avenue, Santa Ana, Cal. 92705. A fiberoptic bundle made from these acrylics is much lighter in weight and much more flexible than the conventional glass fiberoptic bundles now in use. The fiberoptic bundles made from acrylic and used in the preferred embodiment of the present invention are made up of fibers that each have a diameter of approximately 0.010 inches and the overall fiberoptic bundle diameter is approximately 0.100 inches.

While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

I claim:

1. A dental handpiece assembly comprising:
   a) a smooth-walled, aseptic outer tubing having a plurality of integral inner passageways, said inner passageways including a first passageway providing drive air, a second passageway providing an exhaust line, a third passageway providing chip air and a fourth passageway providing coolant water,
   b) a fiberoptic bundle carried within a fifth passageway in the outer tubing, the diameter of the fifth passageway being smaller than an uncompressed diameter of the fiberoptic bundle so that the fiberoptic bundle is compressed and deformed within the fifth passageway to inhibit the twisting of the fiberoptic bundle during use of the handpiece assembly,
   c) a sensing cable carried within a sixth passageway in the outer tubing, and
   d) an adapter for connecting an end of each inner passageway and the fiberoptic bundle to a dental handpiece.

2. The dental handpiece assembly of claim 1 wherein the fiberoptic bundle is made from an acrylic material.

3. The dental handpiece assembly of claim 1 wherein the fiberoptic bundle comprises a plurality of acrylic fibers.

4. The dental handpiece assembly of claim 3 wherein each acrylic fiber has a diameter of approximately 0.010 inches.

5. The dental handpiece assembly of claim 3 wherein the diameter of the fiberoptic bundle is approximately 0.100 inches.

6. The dental handpiece assembly of claim 1 wherein the adapter has a plurality of stems to which are connected each inner passageway.

7. The dental handpiece assembly of claim 1 including means for attaching the sensing cable to the adapter.

8. The dental handpiece assembly of claim 7 wherein the means for attaching the sensing cable to the adapter is an internal passageway in the adapter which terminates in an aperture in the surface of the adapter whereby the sensing cable can be fed through the internal passageway and out the aperture and then wrapped around the adapter to secure the sensing cable thereto.

9. The dental handpiece assembly of claim 7 wherein the adapter is a generally plastic body having a metal sleeve to provide for touch-activation of the fiberoptic bundle.

10. A method of assembling a fiberoptic bundle inside a dental handpiece assembly comprising the steps of:
   (a) providing a smooth-walled, aseptic outer tubing having a plurality of integral inner passageways, at least one of the passageways designed to receive the fiberoptic bundle and the fiberoptic bundle passageway having a normal diameter smaller than an uncompressed diameter of the fiberoptic bundle,
   (b) expanding the fiberoptic bundle passageway to a diameter larger than the uncompressed diameter of the fiberoptic bundle,
   (c) inserting the fiberoptic bundle into the fiberoptic bundle passageway,
   (d) allowing the fiberoptic bundle passageway to return to its normal diameter so that the fiberoptic bundle is compressed and deformed within the fiberoptic bundle passageway to inhibit the twisting of the fiberoptic bundle during use of the handpiece assembly.

11. The method of claim 10 wherein air is used to expand the fiberoptic bundle passageway beyond its normal diameter and the fiberoptic bundle is fed down the fiberoptic bundle passageway while the air is being applied and the air is removed to allow the fiberoptic bundle passageway to return to its normal diameter.

12. A dental handpiece assembly comprising:
 (a) a smooth-walled, aseptic outer tubing having a plurality of integral inner passageways, said inner passageways including a first passageway providing drive air, a second passageway providing an exhaust line, a third passageway providing chip air and a fourth passageway providing coolant water,
 (b) a fiberoptic bundle carried within a fifth passageway in the outer tubing, the diameter of the fifth passageway being smaller than an uncompressed diameter of the fiberoptic bundle so that the fiberoptic bundle is compressed and deformed within the fifth passageway to inhibit the twisting of the fiberoptic bundle during use of the handpiece assembly, and
 (c) an adapter for connecting an end of each inner passageway and the fiberoptic bundle to a dental handpiece.

13. The dental handpiece assembly of claim 12 wherein the fiberoptic bundle is made from an acrylic material.

14. The dental handpiece assembly of claim 12 wherein the fiberoptic bundle comprises a plurality of acrylic fibers.

15. The dental handpiece assembly of claim 14 wherein each acrylic fiber has a diameter of approximately 0.010 inches.

16. The dental handpiece assembly of claim 14 wherein the diameter of the fiberoptic bundle is approximately 0.100 inches.

17. The dental handpiece assembly of claim 12 wherein the adapter has a plurality of stems to which are connected each inner passageway.

* * * * *